United States Patent [19]

Dunks et al.

[11] Patent Number: 4,716,234

[45] Date of Patent: Dec. 29, 1987

[54] ULTRAVIOLET ABSORBING POLYMERS COMPRISING 2-(2'-HYDROXY-5'-ACRYLOYLOXYALKOX-YPHENYL)-2H-BENZOTRIAZOLE

[75] Inventors: Gary B. Dunks, Upland; Akira Yamada, Claremont, both of Calif.; Charles D. Beard, Montchanin, Del.; Namassivaya Doddi, Upland, Calif.

[73] Assignee: Iolab Corporation, Covina, Calif.

[21] Appl. No.: 937,171

[22] Filed: Dec. 1, 1986

[51] Int. Cl.$^4$ .............. C07D 249/16; C08F 232/08; C08F 120/36
[52] U.S. Cl. .................................. 548/259; 548/260; 526/259
[58] Field of Search ............... 548/259, 260; 526/259

[56] References Cited

U.S. PATENT DOCUMENTS 4,220,788 9/1980 Bader et al. .................... 548/259
4,528,311 7/1985 Beard et al. .................... 526/259

FOREIGN PATENT DOCUMENTS 0080663 6/1983 European Pat. Off. ........... 526/259
2835846 2/1979 Fed. Rep. of Germany ...... 548/260
2487994 2/1982 France ............................. 548/259

Primary Examiner—Joseph L. Schofer
Assistant Examiner—Peter D. Mulcahy
Attorney, Agent, or Firm—Charles J. Metz; Wayne R. Eberhardt

[57] ABSTRACT

Ultraviolet light absorbing compositions comprising 2-(2'-hydroxy-5'-acryloyloxyalkoxyphenyl(-2H-benzo-trizoles, and copolymers thereof with one or more other monomers copolyermizable therewith, particularly acrylic monomers, are useful in the manufacture of ocular devices, particularly intraocular lenses and contact lenses.

9 Claims, 2 Drawing Figures

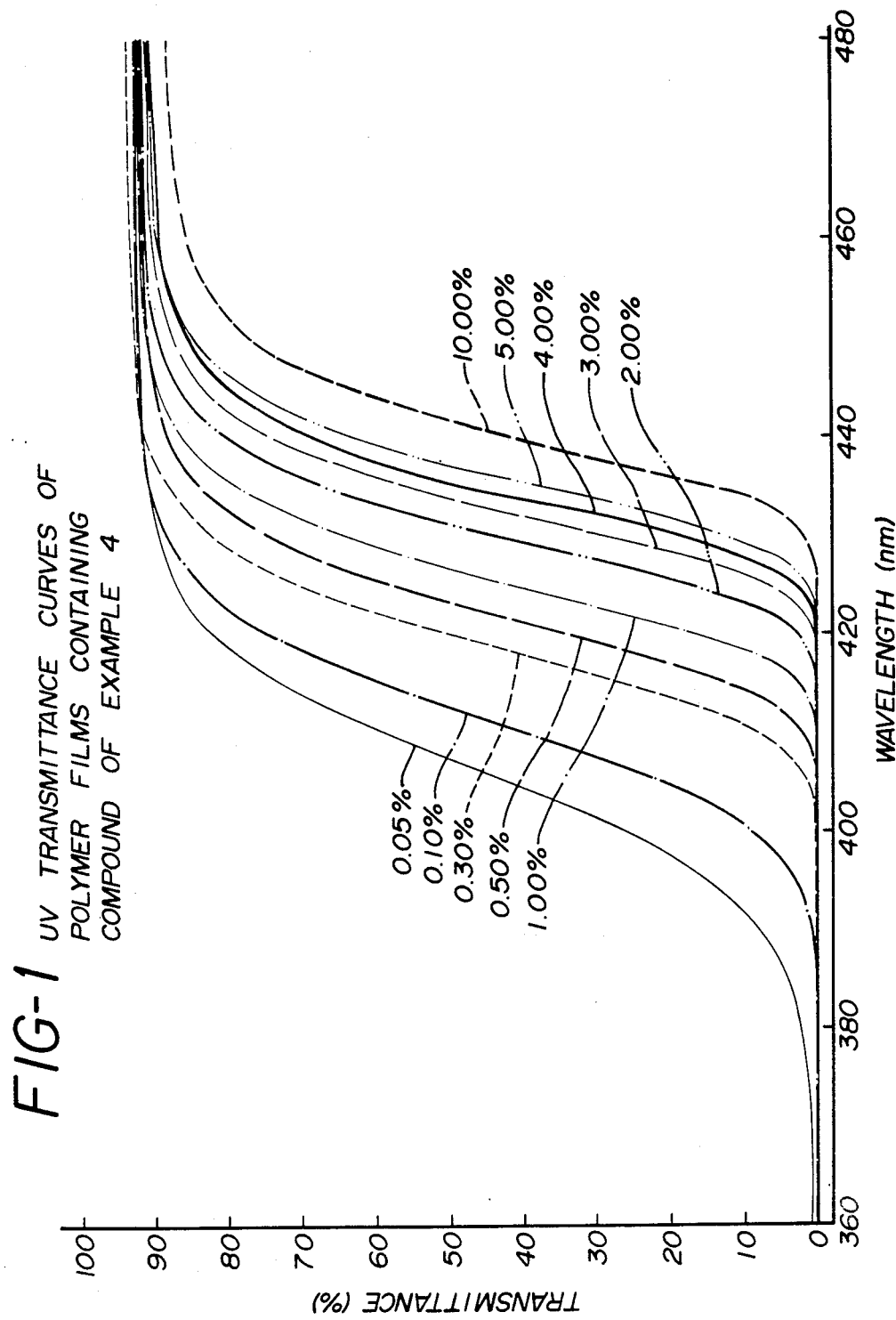

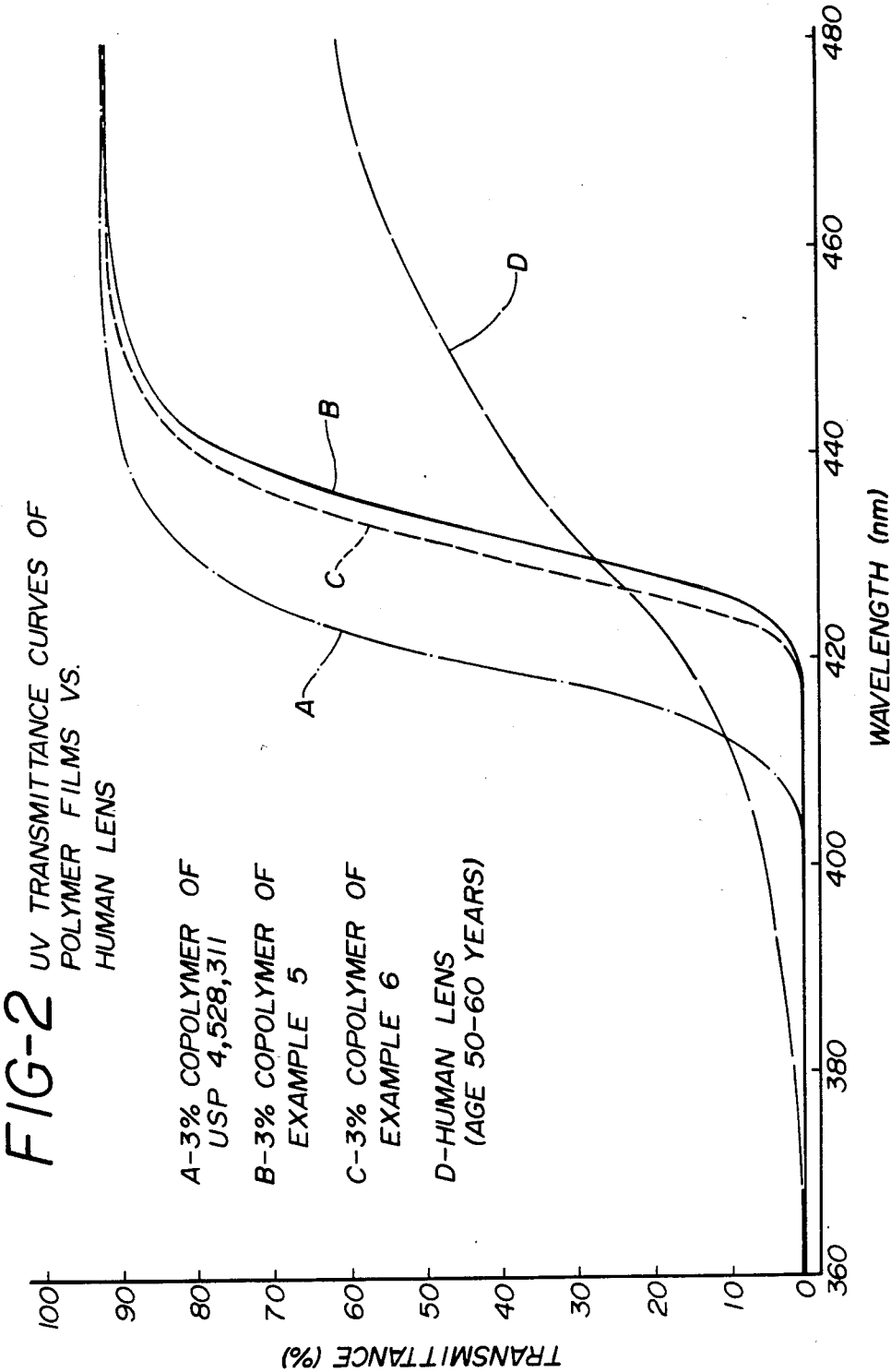

ULTRAVIOLET ABSORBING POLYMERS COMPRISING 2-(2'-HYDROXY-5'-ACRYLOYLOXYALKOXY-PHENYL)-2H-BENZOTRIAZOLE

BACKGROUND OF THE INVENTION

This invention relates to ultraviolet light absorbing polymer compositions, and more particularly, to polymer compositions comprising copolymers of 2-(2'-hydroxy-5'-acryloyloxyalkoxy phenyl)-2H-benzotriazole with one or more other monomers copolymerizable therewith, particularly acrylic monomers. This invention further relates to ocular devices, particularly intraocular lenses and contact lenses, prepared from such ultraviolet light absorbing polymers.

The absorption of radiation in the ultraviolet range by polymeric materials is a major cause of the light-induced degradation therein. It is standard practice to add a low molecular weight UV "stabilizer" to light-sensitive polymers to absorb the light in the destructive range or to quench the energy generated as a result of the excitation of the light-absorbing functional groups in the polymer.

Although low molecular weight UV absorbers or quenchers of various types are effective in inhibiting or retarding the destruction of the polymers to which they are added, their extractibility in various media and/or their volatility during the processing or fabrication of the polymers at elevated temperatures place a limitation on their utility.

This problem has been remedied to a considerable extent by the synthesis of copolymerizable monomers containing structural moieties capable of function as UV absorbers or quenchers. The copolymerization of such monomers results in the formation of copolymers with increased stability, i.e., resistance to degradation upon exposure to UV light with decreased extractibility and volatility. The addition of such polymers to a suitable matrix polymer imparts these properties to the latter.

U.S. Pat. No. 4,304,895 discloses the use of 2-hydroxy-4-methacryloyloxybenzophenone and mixtures thereof as a monomeric ultraviolet light absorber copolymerizable with acrylic monomers and useful in the preparation of UV absorbing hard contact lenses.

Similarly, the copolymerization of an allyl-2-hydroxy-benzophenone with an acrylate ester such as methyl methacrylate is described in U.S. Pat. No. 4,310,650, and, the copolymerization of ethylenically unsaturated derivatives of 2,4-dihydroxy benzophenone with other vinyl type comonomers is broadly disclosed in U.S. Pat. No. 3,162,676.

U.S. Pat. No. 4,528,311 discloses cerain benzotriazole monomers which are copolymerizable with vinyl monomers such as methyl methacrylate to yield optically clear polymers useful in the preparation of intraocular and contact lenses. Representative of the disclosed benzotriazole monomers and a particularly preferred compound is 2-(2'-hydroxy-5'-methacryloyloxypropyl-3'-tert-butylphenyl)-5-chloro-2H-benzotriazole which has the structure

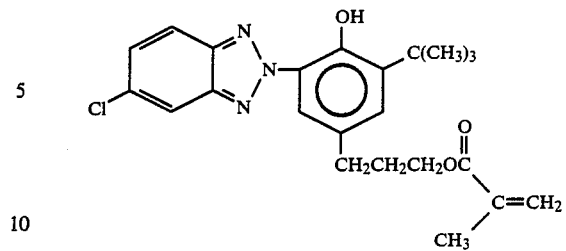

UV absorbing lenses are particularly desirable for use by persons who have had their natural lenses surgically removed due to cataracts or other deterioration of the lens. The visual correction of aphakia resulting from such lens removal requires the use of high plus corrective lens which may be in the form of spectacles, contact lens or intraocular lens.

In the normal eye, a portion of incident light entering the eye is absorbed by various parts of the eye so that only the unabsorbed or transmitted portion strikes the retina. Incident light may comprise the entire spectrum of wavelengths including the ultraviolet, visible and infrared.

The cornea preferentially absorbs the ultraviolet portion of the light with wavelengths up to about 300 nm. The crystalline lens preferentially absorbs ultraviolet light with wavelengths from about 300 up to about 400 nm. The crystalline lens also absorbs a significant portion of the visible light at wavelengths of from 400 to about 450 nm, particularly as the lens ages and develops a yellow tint. In the aphakic eye, where there is no crystalline lens, light from 300 to 450 nm will be transmitted directly to the retina, and the total spectrum of the light striking the retina in the aphakic eye will be different from that in the normal eye. As a consequence, aphakic patients are very sensitive to light in the ultraviolet range and may experience discomfort or color confusion when exposed to natural light or artificial light having high levels of ultraviolet wavelengths.

Intraocular lenses and hard contact lenses are presently produced from methylmethacrylate polymers which exhibit a combination of properties desirable for such products, particularly optical clarity, the capability of being cut and polished to specific optical powers, and chemical inertness. Soft contact and intraocular lenses may be fabricated of silicone or fluorocarbon polymers, or hydrogels such as hydroxymethyl methacrylate and N-vinylpyrrolidone. UV absorbing lenses of polymethylmethacrylate (PMMA) are required to maintain these properties while achieving at least 85% absorption of light to 400 nm based on a polymer film thickness of 1 mm. In addition, absorption should be minimal above 450 nm to avoid excessive yellowing of the lens.

While the benzotriazole monomers described in U.S. Pat. No. 4,528,311 are effective UV absorbers and form chemically stable copolymers with, for example, methyl methacrylate, a concentration of about 3 percent of the monomer in the copolymer is required to provide the desired degree of absorption to 400 nm. The absorption of such copolymers cuts off sharply above 400 nm so that very little light in the 400 to 450 nm range is absorbed. As a consequence, lenses of PMMA copolymers do not demonstrate the same absorption characteristics as the natural lens of an elderly person who is the most frequent recipient of an intraocular lens.

It is accordingly an object of the present invention to provide a copolymer composition with improved UV absorption characteristics. It is a further object to provide a novel UV absorbing monomer material which is copolymerizable with vinyl and silicone monomers. A yet further object is to provide a new composition of matter which, when copolymerized at low concentrations with other monomers, effectively absorbs at least 85% of incident light below 420 nm at 1 mm thickness. It is a further object to provide a new monomeric material which absorbs UV light in the range of 300 to 400 nm more effectively than prior art materials. These and other objects of the present invention will be apparent from the ensuing description and claims.

SUMMARY OF THE INVENTION

There is provided as a new composition of matter 2-(2'-hydroxy-5'-acryloyloxyalkoxyphenyl)-2H-benzotriazoles of the structure

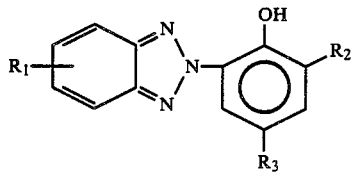

wherein $R_1$ is H, halogen or alkoxy of 1 to 3 carbon atoms, $R_2$ is selected from the group consisting of H, $CH_3$, and t-alkyl of 4 to 6 carbon atoms, and $R_3$ is

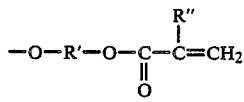

wherein $R'$ is $C_2-C_{10}$ alkylene which may be straight chain or branched, and $R''$ is H, $CH_3$ or $CH_2X$ where X is halogen.

The above defined benzotriazoles are copolymerizable with vinyl monomers such as methyl methacrylate to yield optically clear polymers useful in the preparation of intraocular, contact and spectacle lenses. From 0.01 to about 20% by weight, and preferably from 0.5 to 10% by weight of the benzotriazole compound is incorporated in the copolymer, the minimum effective amount for 85% absorption at 420 nm and 1 mm film thickness depending upon the particular structure of the benzotriazole compound. High molecular weight homopolymers of the benzotriazole monomers may also be prepared and incorporated into a variety of organic materials to impart UV absorption properties thereto.

DESCRIPTION OF THE DRAWINGS

FIG. 1 is a plot of UV transmittance curves for polymethylmethacrylate copolymers with increasing amounts of a benzotriazole monomer of the present invention.

FIG. 2 is a plot of UV transmittance curve for the polymers of the present invention, in comparison with a polymer of the prior art and a human lens.

DETAILED DESCRIPTION OF THE INVENTION

The benzotriazole monomers of the present invention are those compositions defined by the structure

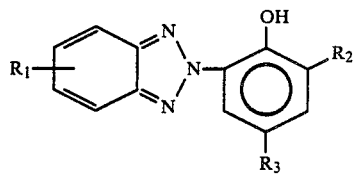

wherein $R_1$ is H, halogen or alkoxy of 1 to 3 carbon atoms, $R_2$ is selected from the group consisting of H, $CH_3$, and t-alkyl of 4 to 6 carbon atoms, and $R_3$ is

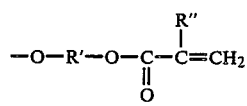

wherein $R'$ is $C_2-C_{10}$ alkylene which may be straight chain or branched, and $R''$ is H, $CH_3$ or $CH_2X$ where X is halogen.

Particularly preferred compositions of the above structure are those where $R_1$ is $CH_3-O-$, $R_2$ is t-butyl, and $R_3$ is a group wherein $R'$ is $-C_2H_4-$ or $-C_3H_6-$ and $R''$ is $CH_3$.

Specifically preferred compounds encompassed by the above formula include:

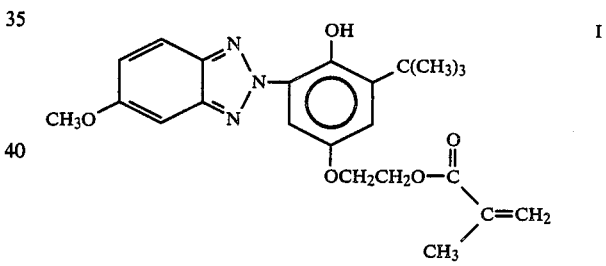

2-[2'-Hydroxy-5'-(β-methacryloyloxyethoxy)-3'-tert-butylphenyl]-5-methoxy-2H-benzotriazole; and

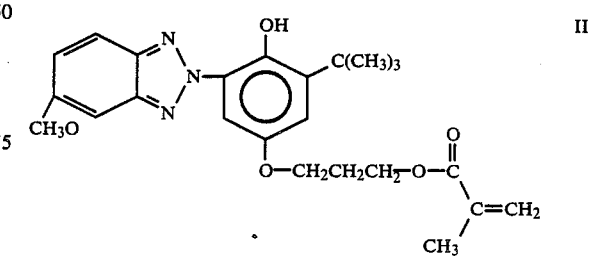

2-[2'-Hydroxy-5'-(γ-methacryloyloxypropoxy)-3'-tert-butylphenyl]-5-methoxy-2H-benzotriazole.

The preparation of the above two specifically preferred compounds, and the copolymerization of these compounds with methyl methacrylate are described in the following examples for purposes of illustration.

EXAMPLE 1

Preparation of Intermediate
2-tert-Butyl-4-(3'-hydroxypropoxy)phenol

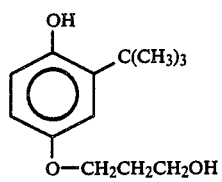

tert-butylhydroquinone, 856.8 g (5 mol) was dissolved in 2.5 L of methanol under argon. To the solution were added 206.2 g (5 mol) of sodium hydroxide, 1 liter (L) of water, 482.3 g (5 mol) of 3-chloro-1-propanol and 6.25 g (0.037 mol) of potassium iodide. The resulting solution was heated at reflux temperature for 20 hours under argon. The reaction mixture was cooled to room temperature, diluted with 5.6 L of water and extracted with methylene chloride (total 4 L). The combined methylene chloride layer was washed with water, dried with anhydrous sodium sulfate and evaporated. The residue was vacuum distilled. The distillate was further purified by recrystallization from toluene (3 mL/g) to give 396 g of pure compound, m.p. 78.5°–80.5° C.

EXAMPLE 2

Preparation of Intermediate
2-tert-Butyl-4-(γ-hydroxypropxy)-6-(4'-methoxy-2'-nitrophenylazo)phenol

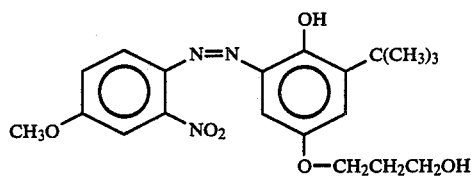

A mixture of 90.6 g (0.53 mol) of 98% 4-methoxy-2-nitroaniline and 180 mL of conc. hydrochloric acid was stirred overnight at room temperature, and diluted with 160 mL of water and 300 g of ice. A solution of 37.7 g (0.53 mol) of 97% sodium nitrite in 140 mL of water was added dropwise to the mixture at −5°∼0° C. After the addition was finished, the mixture was stirred for 1 hour at 0° C. Sulfamic acid was added to destroy excess nitrous acid until KI/Starch test gave a negative result. The mixture was filtered and the filtrate was added dropwise to a stirred solution of 112.2 g (0.5 mol) of the product of Example 1, 60 g of sodium hydroxide and 2 L of water at −5°∼0° C. After approximately ⅓ of the diazonium solution was added, 400 mL of 10% NaOH was added dropwise together to the reaction mixture. Both additions ended at the same time. During the additions, the reaction mixture was kept below 0° C. with external cooling. The reaction mixture was further stirred below 0° C. for 2 hours, then allowed to warm up to room temperature. The azo dye was isolated by acidification with hydrochloric acid, filtration and washing with water, and used without further purification for the next reaction.

EXAMPLE 3

Preparation of Intermediate
2-[2'-Hydroxy-5'-(γ-hydroxypropoxy)-3'-tert-butylphenyl]-5-methoxy-2H-benzotriazole

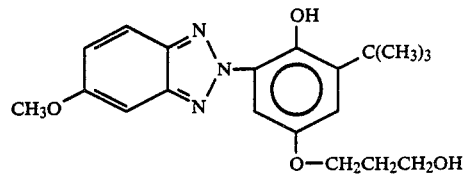

The azo dye of Example 2 was dissolved in 1500 mL of reagent ethanol. A glucose solution (180 g, 1 mol in 1500 mL of aqueous 2N NaOH) was added dropwise to the azo dye solution under argon, at ambient temperature. The reaction temperature was kept below 30° C. The mixture was stirred overnight. To the homogeneous reaction mixture was added freshly activated zinc dust (165 g of zinc dust was washed with 1N HCl and water successively and dried by suction) in portions. The mixture was stirred at room temperature (18°–30° C.) for 3 hours and diluted with 1000 mL of water. After 15 minutes, the stirring was discontinued and the mixture was allowed to stand for 1 hour. The resulting precipitate was separated by filtration and washed with water. The filter cake was extracted with hot reagent alcohol (total 2 L) until only zinc remained in the solid residue. The extract was cooled to room temperature. The resulting crystals were separated by filtration, washed with cold reagent alcohol and dried in vacuo to give 67.8 g of crude product. The crude product was dissolved in 4 L of boiling heptane and the resulting solution was filtered. From the solution 99.5% pure material was obtained. Yield 60 g (32%) m.p. 128°–130° C.

EXAMPLE 4

Preparation of Monomer
2-[2'-Hydroxy-5'-(γ-methacryloyloxypropoxy)-3'-tert-butylphenyl]-5-methoxy-2H-benzotriazole

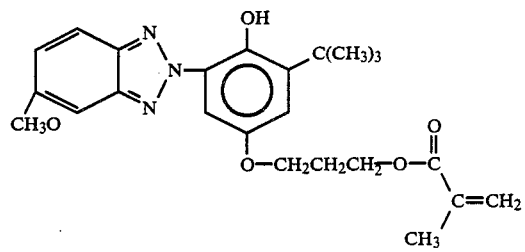

In a 2 L flask equipped with a mechanical stirrer, a thermometer and an addition funnel which was protected from moisture with a drying tube were placed 37.16 g (0.1 mol) of the benzotriazole of Example 3, 800 mL of dry toluene and 17 mL (0.21 mol) of dry pyridine. A solution of 13 mL (0.128 mol) of methacryloyl chloride (freshly distilled) in 10 mL of toluene was added to the mixture over 30 minutes. The reaction mixture was stirred overnight at room temperature (<25° C.). A white precipitate (pyridinium chloride) was separated by filtration and washed with toluene. The filtrate and washings were combined, washed with 1N hydrochloric acid, water, aqueous sodium bicarbonate and water successively, then dried with anhydrous sodium sulfate and evaporated. The residue (ca. 41 g) was dissolved in a mixture of 1 L of methanol and 500 mL of methylene chloride by heating in a water bath at 45° C. The resulting solution was filtered to remove a small amount of insoluble materials and diluted with 250 mL of methanol. The solution was cooled slowly at room temperature, in a refrigerator and finally then placed in a freezer where the temperature was reduced to about −5° C. The resulting crystals were separated by filtration, washed with 250 mL of cold methanol/methylene chloride (90/10 v/v) and dried in vacuo to give 38.4 g of 99.7% pure product m.p. 114°–116° C.

EXAMPLE 5

Polymerization

A Pyrex polymerization tube was charged with 0.60 g of the product of Example 4, 2.00 g of ethyl acrylate, 17.40 g of methyl methacrylate, 111 μL of 1-dodecanethiol, 0.12 g of stearic acid and 25.0 mg of lauroyl peroxide, flushed with argon and sealed. The mixture was polymerized at 60° C. for 72 hours. The resulting polymer was further heated at 130° C. for 4 hours and hot pressed into 1-mm-thick film. GPC analysis of the polymer showed that the UV absorbing benzotriazole moiety was chemically bonded in the polymer matrix. The film showed transmission of 92.7% at 700 nm, 29.0% at 430 nm and 0.08% at 400 nm.

Following the procedure of Examples 1–4, the monomer 2-[2'-hydroxy-5'-($\beta$-methacryloyloxyethoxy)-3'-tert-butylphenyl]-5-methoxy-2H-benzotriazole was prepared utilizing 2-tert-butyl-4-(2'-hydroxyethoxy)phenol as a starting intermediate. Other benzotriazole monomers within the scope of the present invention are prepared in a like manner.

EXAMPLE 6

Polymerization

A Pyrex test tube was charged with 0.75 g of 2-[2'-hydroxy-5'-($\beta$-methacryloyloxyethoxy)-3'-tert-butylphenyl]-5-methoxy-2H-benzotriazole, 2.00 g of ethyl acrylate 22.25 g of methyl methacrylate, 89 μL of 1-dodecanethiol, 0.15 g of stearic acid and 8.2 mg of azobisisobutyronitrile, flushed with argon and then sealed. The mixture was polymerized at 70° C. for 18 hours. The resulting polymer was hot pressed into 1-mm-thick film. The film showed transmission of 93.1% at 700 nm, 36.7% at 430 nm and 0.08% at 400 nm. A UV transmission curve for the polymer of this example is plotted in FIG. 2.

A UV-transmittance curve for the polymer of Example 5 containing 3 percent by weight of the benzotriazole of Example 4 is presented in FIG. 1, together with curves of similarly prepared polymers containing from 0.05 to 10.0 percent of the compound of Example 4. With reference to FIG. 1, the copolymer compositions are seen to absorb strongly up to about 400 nm at concentrations of as little as 0.10% by weight of the benzotriazole in polymethylmethacrylate. As the concentration of the benzotriazole is increased, substantially complete absorption occurs up to about 430 nm at 10% concentration. The wavelength at which the absorbence cuts off may accordingly be predetermined within the range of from about 390 to 430 nm by regulating the amount of UV absorber included in the composition.

For optical uses, particularly contact lenses and intraocular lenses for aphakic patients who have had their natural lens removed, strong absorption of light up to about 420 nm is desired. In the case of the compound of Example 4, from about 1 to 5 percent concentration, and particularly from about 2 to 3 percent concentration, is desirable for such optical applications.

FIG. 2 presents UV transmittance curves of polymer films of Examples 5 and 6 containing 3 percent of the designated benzotriazole for comparison with a copolymer of methylmethacrylate containing 3% of 2-(2'-hydroxy-5'-methacryloyloxypropyl-3'-tert-butylphenyl)-5-chloro-2H-benzotriazole, the copolymerizable UV absorbing monomer of U.S. Pat. No. 4,528,311, and in comparison with the transmittance characteristics of the natural lens of a human patient aged 50–60 years.

With reference to the curves of FIG. 2, it is seen that the transmittance characteristics of the composition of the present invention more closely approaches that of the human lens, with significant absorption occuring in the near UV range of 400 to 420 nm. It is also apparent that the benzotriazoles of the present invention are far more efficient UV light absorbers than those of the prior art reference. For example, the transmittance curve for 0.3% of the compound of Example 4 as shown in FIG. 1 is very close to the transmittance curve for a polymer containing 3% of the benzotriazole of U.S. Pat. No. 4,528,311.

The benzotriazoles of the present invention may be copolymerized with any of a number of unsaturated monomers to provide polymeric compositions having desirable UV absorbing characteristics. Alternatively, homopolymers or copolymers of the benzotriazoles of the present invention may be utilized as additives to a wide variety of organic polymers to provide UV absorption properties. Representative of the polymers and copolymers useful in conjunction with the benzotriazole monomers and polymers of the present invention are:

a. Polymers which are derived from mono- or diolefins, e.g., polyethylene which can optionally be cross-linked polypropylene, polyisobutylene, polymethylbutene-1, polymethylpentene-1, polyisoprene, polybutadiene.

b. Mixtures of the homopolymers cited under (a), for example mixtures of polypropylene and polyethylene, polypropylene and polybutene-1, polypropylene and polyisobutylene.

c. Copolymers of the monomers based on the homopolymers cited under (a), for example ethylene/propylene copolymers, propylene/butene-1 copolymers, propylene/isobutylene copolymers, ethylene/butene-1 copolymers as well as terpolymers of ethylene and propylene with a diene, for example hexadiene, dicyclopentadiene or ethylidene norbornene, and copolymers of α-olefins, e.g., ethylene with acrylic or methacrylic acid.

d. Polystyrene.

e. Copolymers of styrene and of α-methylstyrene, for example styrene/butadiene copolymers, styrene/acrylonitrile copolymers, styrene/acrylonitrile/methacrylate copolymers, styrene/acrylonitrile copolymers modified with acrylic ester polymers to provide impact strength as well as block copolymers, e.g., styrene/butadiene/styrene block copolymers.

f. Graft copolymers of styrene, for example the graft polymer of styrene to polybutadiene, the graft polymer of styrene with acrylonitrile to polybutadiene as well as mixtures thereof with the copolymers cited under (e), commonly referred to as acrylonitrile/butadiene/styrene or ABS plastics.

g. Silicone polymers such as the soft hydrophilic polysiloxanes disclosed in U.S. Pat. No. 4,259,467 and the hard polyorganosiloxanes disclosed in U.S. Pat. No. 4,355,147.

h. Halogen-containing vinyl polymers, for example polyvinyl chloride, polyvinylidene chloride, polyvinyl fluoride, chloropolychloroprene, chlorinated rubbers, vinyl chloride/vinylidene chloride copolymers, vinyl chloride/vinyl acetate copolymers, vinylidene chloride/vinyl acetate copolymers.

i. Polymers which are derived from $\alpha,\beta$-unsaturated acids and derivatives thereof, polyacrylates and polymethacrylates, polyhydroxyethylmethacrylate, polyacrylic amides and polyacrylonitrile. The instant compounds are advantageously used in heat-curable acrylic resin lacquers which are composed of a copolymer of acrylic acid and one or more of its derivatives, and a melamine-formaldehyde resin.

j. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.

k. Homopolymers and copolymers which are derived from epoxides, for example polyethylene oxide or the polymers which are derived from bis-glycidyl ethers.

l. Polyacetals, for example polyoxymethylene, as well as polyoxymethylenes which contain ethylene oxide as comonomer.

m. Polyalkylene oxides, for example polyoxyethylene, polypropylene oxide or polybutylene oxide.

n. Polyphenylene oxides.

o. Polyurethanes and polyureas, such as in urethane coatings.

p. Polycarbonates.

q. Polysulfones.

r. Polyamides and copolyamides which are derived from diamines and dicarboxylic acids and/or from aminocarboxylic acids or the corresponding lactams, for example polyamide 6, polyamide 6/6, polyamide 6/10, polyamide 11, polyamide 12, n-vinyl lactams and poly-m-phenylene-isophthalamide.

s. Polyesters which are derived from dicarboxylic acids and dialcohols and/or from hydroxycarboxylic acids or the corresponding lactones, for example polyethylene glycol terephthalate, poly-1,4-dimethylolycyclohexane terephthalate.

t. Crosslinked polymers which are derived from aldehydes on the one hand and from phenols, ureas and melamine on the other, for example phenol/formaldehyde, urea/formaldehyde and melamine/formaldehyde resins.

u. Alkyd resins, for example glycerol/phthalic acid resins and mixtures thereof with melamine/formaldehyde resins.

v. Unsaturated polyesters resins which are derived from copolyesters of saturated and unsaturated dicarboxylic acids with polyhydric alcohols as well as from vinyl compounds as crosslinking agents and also the halogen-containing, flame-resistant modifications thereof.

w. Natural polymers, for example cellulose, rubber, as well as the chemically modified homologous derivatives thereof, for example cellulose acetates, cellulose propionates and cellulose butyrates and the cellulose ethers, for example methyl cellulose.

Particularly useful compositions are copolymers comprising from 0.5 to 20% by weight of benzotriazoles of the present invention with other ehylenically unsaturated materials such as styrene, methylstyrene, siloxanes, acrylates, methacrylates, acrylamide, acrylonitrile, methacrylonitrile, vinylacetate, vinylidene chloride, vinyl chloride, vinyl fluoride, vinyl lactams ethylene, propylene, and mixtures thereof.

The homopolymers and copolymers of the benzotriazoles of the present invention find wide application in formulating UV absorbing plastics and other organic materials wherever such materials are exposed to UV radiation from either natural or artificial sources. In addition to the medical use in intraocular and contact lenses described above, the materials of the present invention are useful in many industrial applications such as in solar energy collectors, polymeric coatings, transparent plastic films, fluorescent light diffusers, packaging materials, vinyl window coverings, automobile paints and interior coverings, epoxys, fiberglass constructions and the like. Many other applications will be readily apparent to those familiar with this art as a result of proceeding specification.

We claim:

1. A compound of the formula

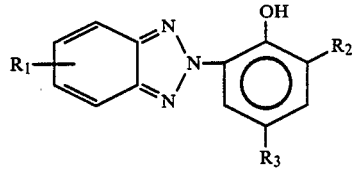

wherein $R_1$ is H, halogen or alkoxy of 1 to 3 carbon atoms, $R_2$ is selected from the group consisting of H, $CH_3$, and t-alkyl of 4 to 6 carbon atoms, and $R_3$ is

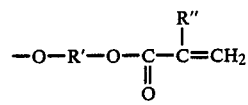

wherein R' is $C_{2-10}$ alkylene which may be straight chain or branched, and R'' is H, $CH_3$ or $CH_2X$ where X is halogen.

2. The compound of claim 1 wherein $R_1$ is $-OCH_3$.

3. The compound of claim 1 wherein $R_2$ is t-butyl.

4. The compound 2-[2'-hydroxy-5'-($\beta$-methacryloyloxyethoxy)-3'-tert-butylphenyl]-5-methoxy-2H-benzotriazole.

5. The compound 2-[2'-hydroxy-5'-($\gamma$-methacryloyloxypropoxy)-3'-tert-butylphenyl]-5-methoxy-2H-benzotriazole.

6. An ultraviolet absorbing composition comprising a polymeric material and from 0.01 to 20% by weight of a benzotriazole compound of claim 1.

7. The composition of claim 6 wherein said polymeric material is selected from the group consisting of polyvinyl halides, polyacrylates, polystyrene, polyvinylidene halides, polycarbonates and acrylonitrile-butadiene-styrene terpolymers.

8. A plastic film comprising the composition of claim 6.

9. A coating material comprising the composition of claim 6.

* * * * *